(12) United States Patent
Katoh et al.

(10) Patent No.: US 7,559,909 B2
(45) Date of Patent: Jul. 14, 2009

(54) WALKING ASSISTANCE DEVICE

(75) Inventors: Hisashi Katoh, Wako (JP); Takashi Hirata, Wako (JP)

(73) Assignee: Honda Motor Co., Ltd., Minato-Ku, Tokyo (JP)

( * ) Notice: Subject to any disclaimer, the term of this patent is extended or adjusted under 35 U.S.C. 154(b) by 0 days.

(21) Appl. No.: 10/557,731

(22) PCT Filed: Mar. 15, 2004

(86) PCT No.: PCT/JP2004/003408

§ 371 (c)(1),
(2), (4) Date: Jun. 23, 2006

(87) PCT Pub. No.: WO2004/103249

PCT Pub. Date: Dec. 2, 2004

(65) Prior Publication Data

US 2007/0106190 A1    May 10, 2007

(30) Foreign Application Priority Data

May 21, 2003    (JP)    ............... 2003-143509

(51) Int. Cl.
*A61F 5/00*    (2006.01)
(52) U.S. Cl. .............. 602/16; 602/23; 602/26; 602/27
(58) Field of Classification Search .......... 602/5, 602/16, 19, 23, 26, 27; 482/66, 124; 607/48, 607/49; 601/5
See application file for complete search history.

(56) References Cited

U.S. PATENT DOCUMENTS

| 5,020,790 | A | * | 6/1991 | Beard et al. .................. 482/4 |
| 5,476,441 | A | * | 12/1995 | Durfee et al. ................. 602/23 |
| 6,589,195 | B1 | * | 7/2003 | Schwenn et al. .............. 602/23 |
| 7,153,242 | B2 | * | 12/2006 | Goffer ......................... 482/66 |

FOREIGN PATENT DOCUMENTS

| JP | 32-10792 | 12/1957 |
| JP | 61-228854 | 8/1968 |
| JP | 58-41556 | 9/1983 |

(Continued)

*Primary Examiner*—Michael A. Brown
(74) *Attorney, Agent, or Firm*—Squire, Sanders & Dempsey, LLP

(57) ABSTRACT

In order to achieve a walking assistance device that can be securely fitted to the user's body while allowing a certain degree of freedom, a walking assistance device is provided comprising a hip joint rotational force generator (hip joint actuator 10) mounted on a side of a hip joint and a knee joint rotational force generator (knee joint actuator 26) mounted on a side of a knee joint to provide an assisting force to a movement of a lower limb, wherein the hip joint rotational force generator is fitted to the body via a first linkage means (link plate 30) having at least two degrees of freedom, and wherein the hip joint rotational force generator and the knee joint rotational force generator are connected to each other via a second linkage means (link bar 25) having an expandable and contractable means. In this way, deformation in lateral and torsional directions of the first linkage means and expansion/contraction of the second linkage means can absorb a deviation in position between the joints of the user's body and the assisting force generators.

7 Claims, 6 Drawing Sheets

FOREIGN PATENT DOCUMENTS

| | | |
|---|---|---|
| JP | 58-163364 | 9/1983 |
| JP | 60-199450 | 8/1985 |
| JP | 60-199450 | 10/1985 |
| JP | 61-228854 | 10/1986 |
| JP | 01-097456 | 4/1989 |
| JP | 6-114089 | 4/1994 |
| JP | 61-014089 | 4/1994 |
| JP | 2001-214303 | 8/2001 |

* cited by examiner

WALKING ASSISTANCE DEVICE

TECHNICAL FIELD

The present invention relates to a walking assistance device for providing an assisting force to the movement of the hip joint or knee joint.

BACKGROUND ART

Various proposals have been made for a walking assistance device that is adapted to mount an actuator to the hip joint or knee joint of a person having a walking impediment due to injury, disease or weakened muscle resulting from aging, so that the power from the actuator can be used to assist the movement of the lower limb.

Conventionally, in such a walking assistance device, it was necessary to fasten corset-like support members onto the hip, thigh and lower leg portions to securely mount rotational actuators on a side of the hip joint and knee joint and transmit the drive torque from the rotational actuators to the lower limb.

However, the prior art devices, such as those disclosed in Japanese Patent Application Laid-Open Publication No. 58-163364 (FIGS. 1-4), are designed mainly for the purpose of securely mounting the actuators to the body, and tend to hamper free movements of the body. Further, because it is impossible to three-dimensionally coincide the position of joints of the human body and the support member, as shown in FIG. 6, for example, an offset existing between the center of the hip joint and the actuator mounted on a side of the hip joint causes a difference E in the motion between the human body and the support member when the leg is swung in a lateral direction. For this reason, in the example of FIG. 6, it is quite difficult to mount a knee joint actuator to the leg so as to be capable of following the lateral movement of the thigh around the hip joint.

DISCLOSURE OF THE INVENTION

In view of such problems of the prior art, a primary object of the present invention is to provide a walking assistance device that can be securely fitted on the body while allowing a certain degree of freedom.

According to the present invention, such an object can be accomplished by providing a walking assistance device comprising a hip joint rotational force generator (hip joint actuator 10) mounted on a side of a hip joint and a knee joint rotational force generator (knee joint actuator 26) mounted on a side of a knee joint to provide an assisting force to a movement of a lower limb, wherein the hip joint rotational force generator is fitted on a body via a first linkage means (link plate 30) having at least two degrees of freedom, and wherein the hip joint rotational force generator and the knee joint rotational force generator are connected to each other via a second linkage means (link bar 25) having an expandable and contractable means.

In this way, deformation in lateral and torsional directions, for example, of the first linkage means and expansion/contraction of the second linkage means can absorb a deviation in position between the joints of the user's body and the assisting force generators.

Preferably, the expandable and contractable means comprises a spring means supporting a weight of the knee joint rotational force generator and component parts below the knee joint rotational force generator. In this way, the knee joint rotational force generator and the component parts below it can be pulled up toward the hip so that the force imposed upon the lower leg portion can be reduced and inadvertent slip of the support member fitted on the lower leg portion can be prevented.

Particularly, it is preferable that the first linkage means consists of a flexible member accommodating a positional deviation of the hip joint rotational force generator in a direction of an arc which is tangential to a rotation center axis of the hip joint rotational force generator, and in a torsional direction around an axis perpendicular to the rotation center axis of the hip joint rotational force generator. This can allow the hip joint rotational force generator to be mounted to the body so as to be able to follow the torsional movements as well as fore and aft or right and left swinging movements of the hip joint.

Further preferably, an axis of deformation of the flexible member crosses the rotation center axis of the hip joint rotational force generator. This can minimize a deviation of motion of the hip joint rotational force generator with respect to the motion of the hip joint.

BEST MODE FOR CARRYING OUT THE INVENTION

Figure 1:
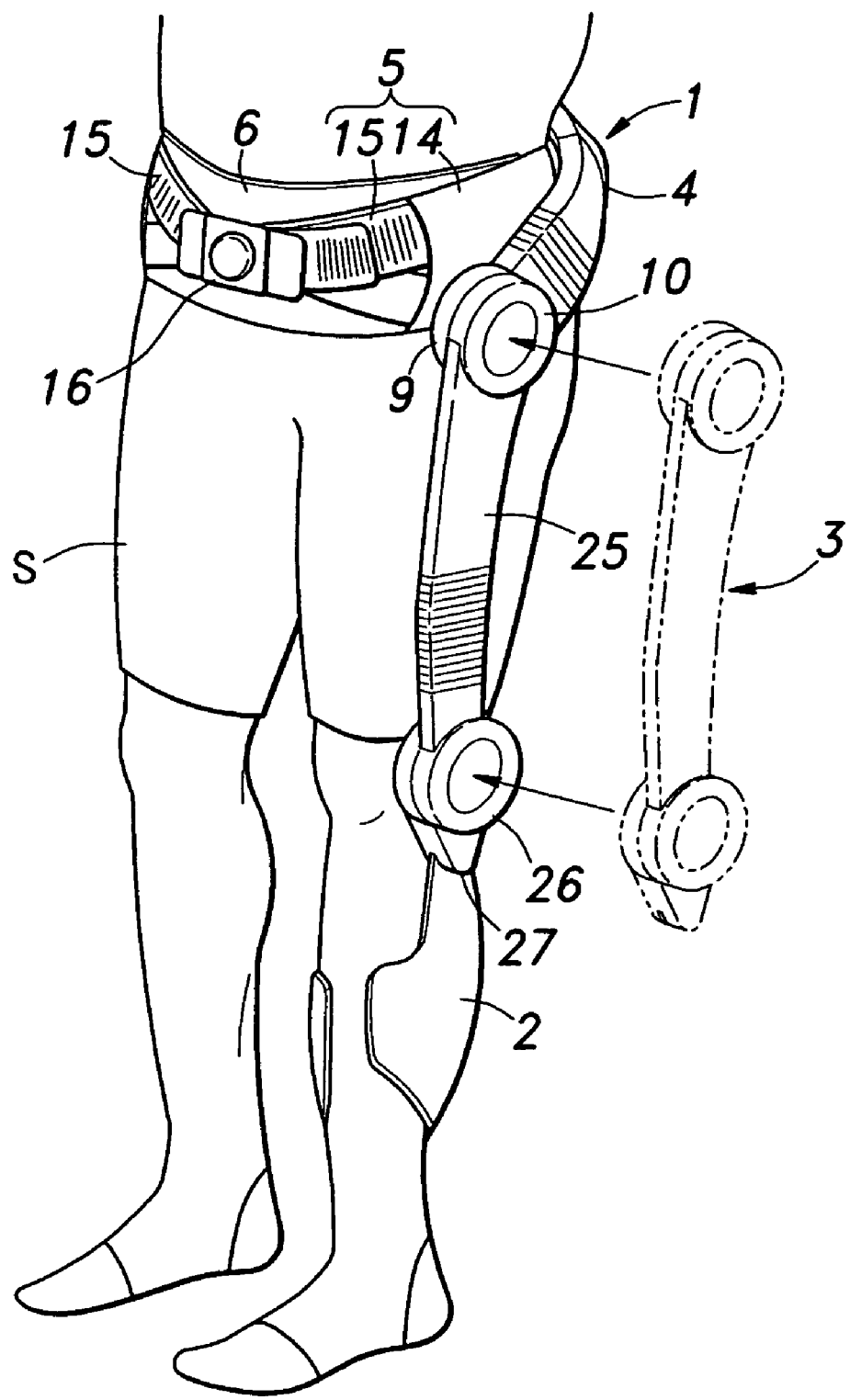
FIG. 1 is a perspective view showing a lower body on which a walking assistance device of the present invention is fitted.

FIG. 1 shows a walking assistance device of the present invention as worn on a user's body. The walking assistance device consists of a hip support member 1, lower leg support member 2 and a drive unit 3, where the hip support member 1 and the lower leg support member 2 are secured on a lower limb and a rotational torque generated by the drive unit 3 is transmitted to the lower limb via the hip and lower leg support members, to whereby provide a force for supplementing a reduced muscle power.

Figure 2:
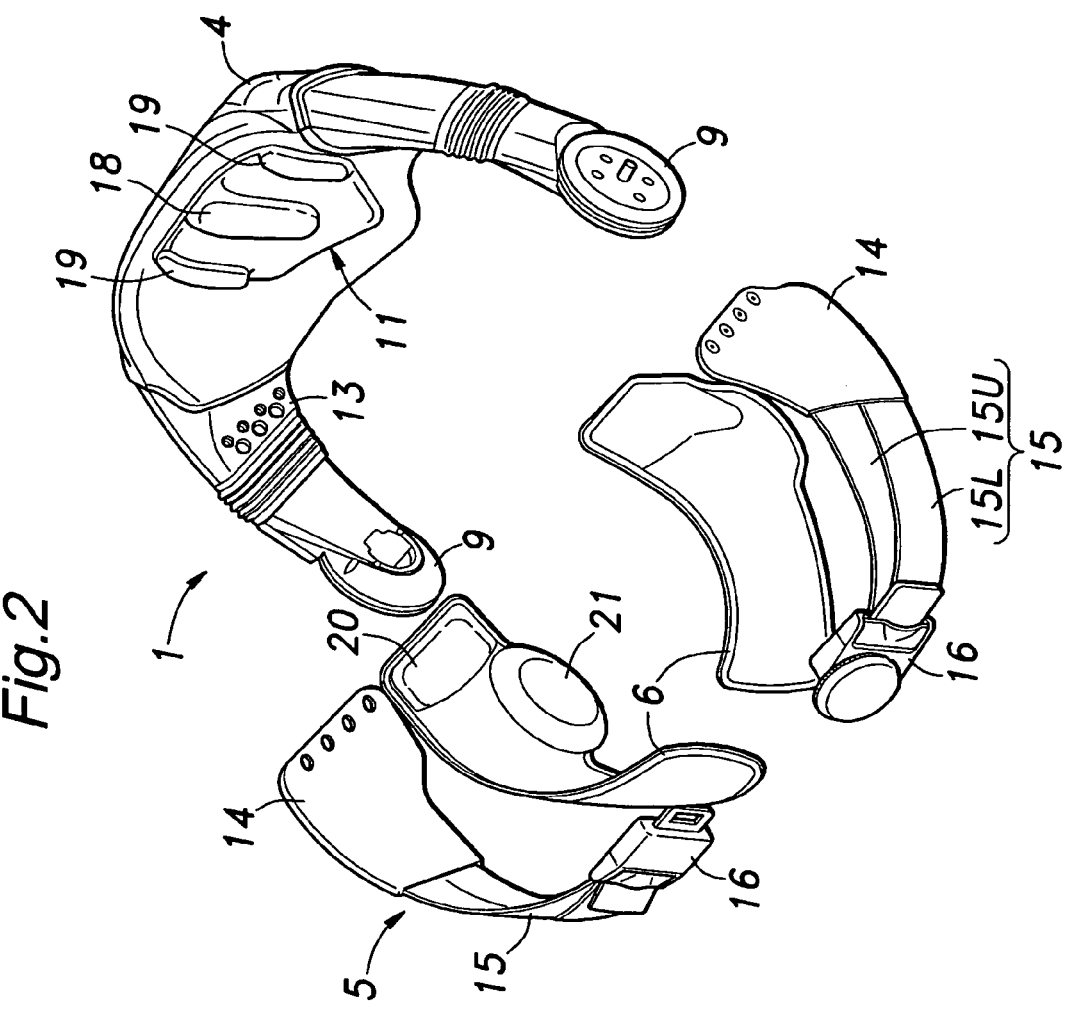
FIG. 2 is an exploded perspective view showing the structure of a hip support member of the walking assistance device according to the present invention.

The hip support member 1 comprises a back support 4, belt portion 5 and lining portion 6, as shown in FIG. 2.

Figure 3:
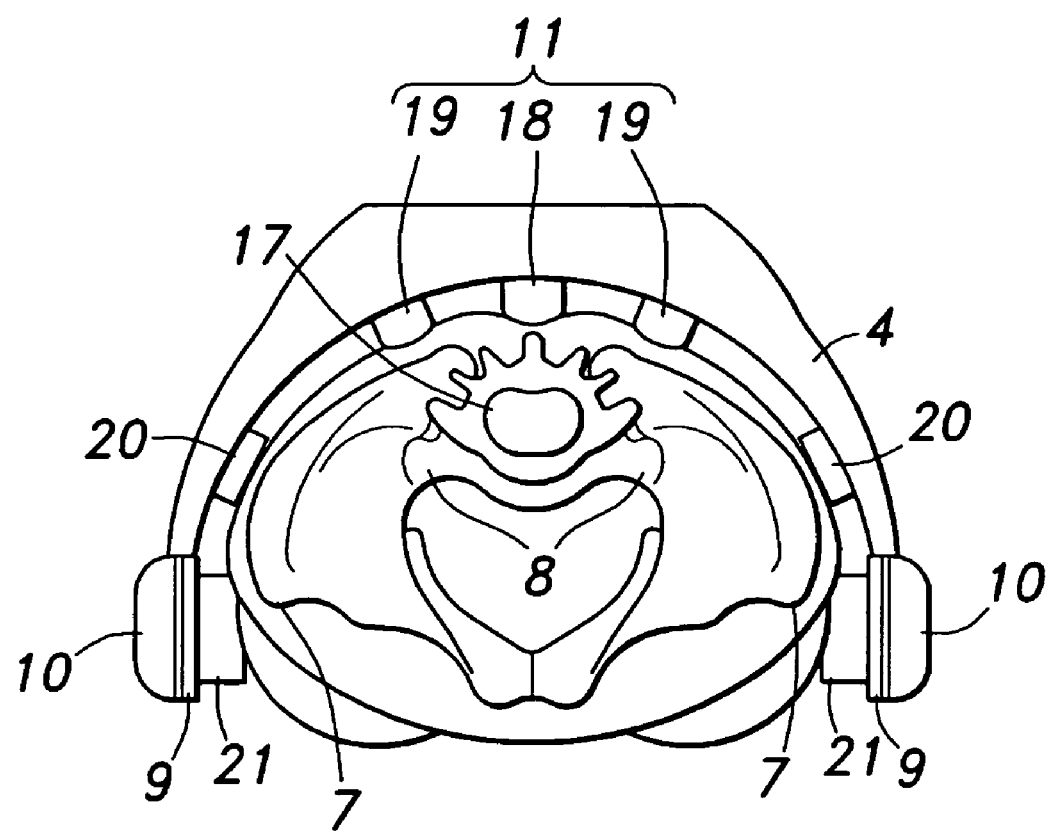
FIG. 3 is an explanatory drawing showing the relationship between a back support and the user's body.

Additionally referring to FIG. 3, the back support 4 is substantially of the shape of letter-U as seen in plan view so that it abuts a region of the body extending from right and left iliac crests (front ends of the pelvic bone) 7 to the backside of the sacroiliac joint (joint between the vertebrae and pelvic bone) 8, and consists of a substantially rigid body so as to withstand the drive force generated by a hip joint actuator 10, which consists of an electric motor equipped with a reduction gear or the like and is mounted on a hip drive source mount 9 provided at each of the right and left ends of the back support 4. A rear portion of the back support 4 has a hollow space so that a control circuit and a battery for supplying electric power to the control circuit as well as to the electric motor are accommodated therein, though not explicitly shown in the drawings. Further, at a portion of the back support 4 that directly abuts the user's body is provided a cushioning pad 11.

The belt portion 5 is made of a relatively rigid material and comprises: a pair of right and left bases 14 integrally attached by means of bolts to inner sides of belt joints 13 provided at right and left side portions of the back support 4; a pair of right and left web parts 15 fixed to front ends of the bases 14; and a pair of right and left buckles 16 attached to front ends of the web parts 15. The inner surface of the belt portion 5, i.e., the surface facing the hip portion of the user's body, is adapted to be attached with the lining portion 6 for protection by means of loop and hook fastener or the like.

The cushioning pad 11 provided to the back support 4 comprises a center pad 18 abutting a depression extending along a lumbar vertebra 17 and a pair of side pads 19 abutting laterally outer regions of erector spinae muscles slightly jutting out backward at right and left of the lumbar vertebra 17. Further, the lining portion 6 comprises iliac pads 20 abutting the iliac crests 7. Thus, a total of five pads abut principal portions of the hip to keep the back support 4 from moving out of place. Further, because direct contact of the hip drive source mount 9 with the user's body would cause pain to the user and could impart a large impact on the body if the user happens to fall, hip joint pads 21 are provided to the lining portion 6 so as to be interposed between the user's body and the hip drive source mount 9 and reduce the impact and pain.

Each of the web parts 15 comprises a pair of upper and lower plain weave belts secured to the associated base 14, and the front ends of the belts are joined together and attached to the corresponding buckle 16 so that they form a shape of letter-V that converges in the front direction. The upper belt 15U of each web part 15 extends from the joint with the base 14 disposed at a position corresponding to the iliac crest 7 toward the buckle 16 disposed at an intermediate portion ("tanden") between the navel and pubic bone along a direction of the extension of muscle fibers of the abdominal external oblique muscle. The lower belt 15L of the web part 15 extends from the joint with the base 14 disposed on a side of the hip joint toward the buckle 16 along a direction of fibers of the abdominal internal oblique muscle.

The upright posture of the spine is maintained by the balance of back muscle, pectoral muscle and abdominal muscle. The weakening of muscles of a person having walking impediment applies not only to the muscles of lower limb but also to the back, pectoral or abdominal muscles. Particularly, the weakening of the abdominal muscle can lower the abdominal cavity and cause the spine to bend in the shape of letter-S as seen in side view, thus making it difficult to maintain the upright posture during walking. According to the device of the present invention, the buckle 16 is positioned at a center of lower abdomen called "tanden" where the rectus abdominis muscle, abdominal external oblique muscle, abdominal internal oblique muscle, transversus abdominis muscle, etc. which play an important role in keeping the upright posture, overlap each other, and a tightening force is applied to the web parts 15 so that the back support 4 fitted on a region extending from the right and left iliac crests 7 to the backside of the secroiliac joint functions to correct the curve of the spine and stabilize the pelvis to achieve a proper posture and at the same time increase the abdominal cavity pressure to lift up the viscera to proper positions. Further, because the web parts 15 abut the lower abdominal portion with a relatively large contact area, the pressure applied to the abdominal cavity can be distributed evenly over the whole lower abdominal portion, thus reducing the uncomfortable pressure felt by the user.

Figure 4:
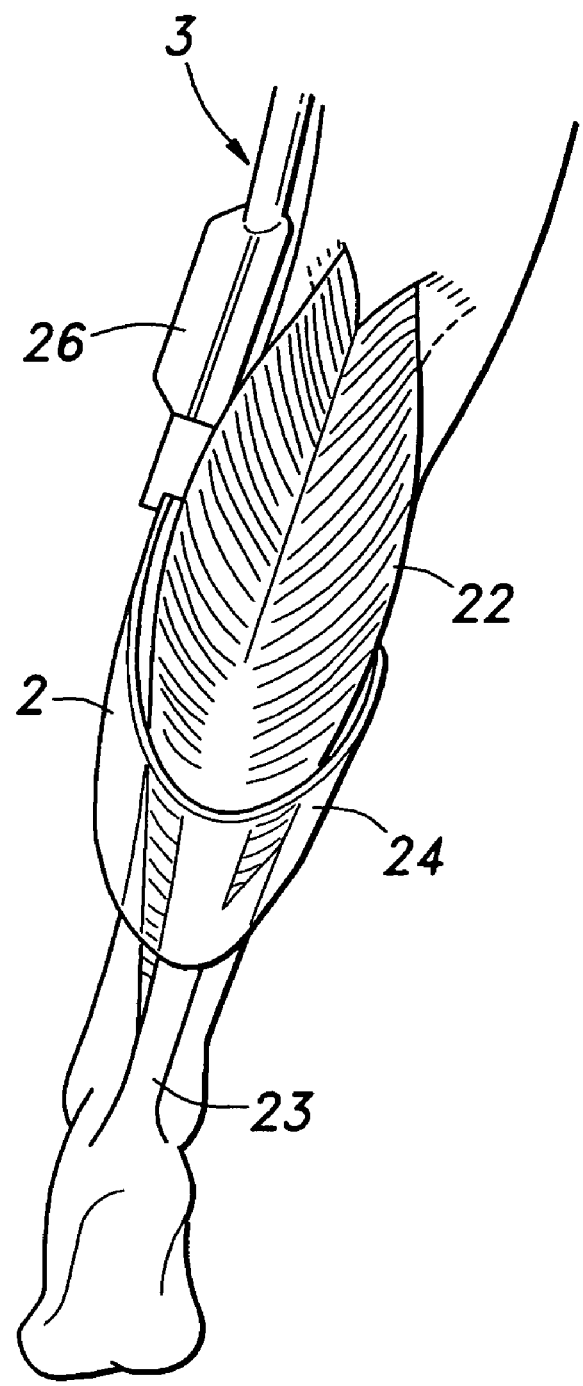
FIG. 4 is an explanatory drawing showing a lower leg support member fitted on a lower leg portion.

On the other hand, as also shown in FIG. 4, the lower leg support member 2 comprises a band-like member 24 wound around the region where the skin movement is relatively small during motion of the lower limb joints, i.e., region extending from lateral sides of an upper part of the anterior tibial muscle to the portion between a lower part of the calf muscle 22 and an upper part of the Achilles tendon 23. According to such a structure, it can be avoided to place the principal engagement points of the lower leg support member 2 on the calf, of which circumferential length can vary with the extension/flexion of the knee, or on the Achilles tendon where the skin moves with the motion of the ankle, and therefore it is possible to securely fasten the lower leg support member 2 on the lower leg with an abundant tightening force.

Figure 5:
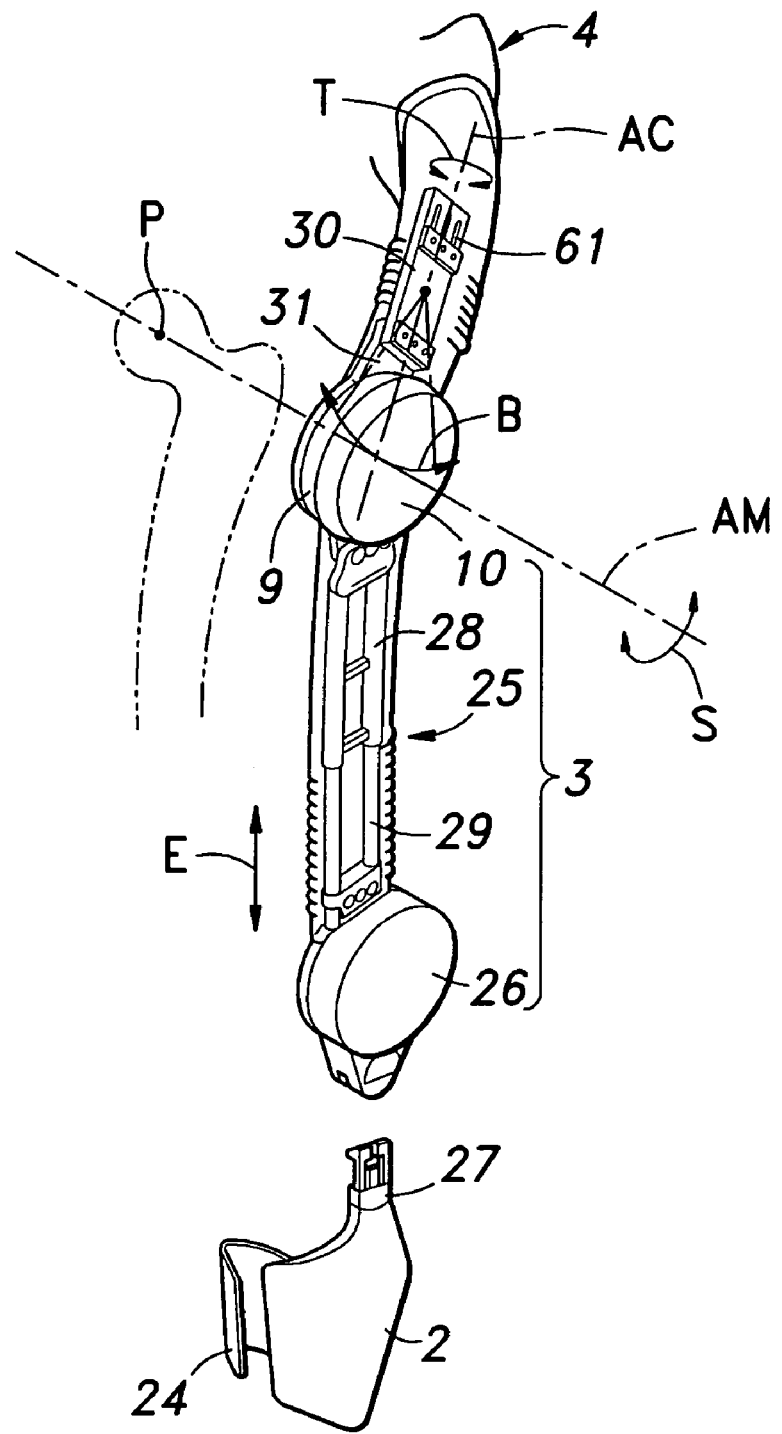
FIG. 5 is a perspective view of a principal part of the walking assistance device of the present invention.
Figure 6:
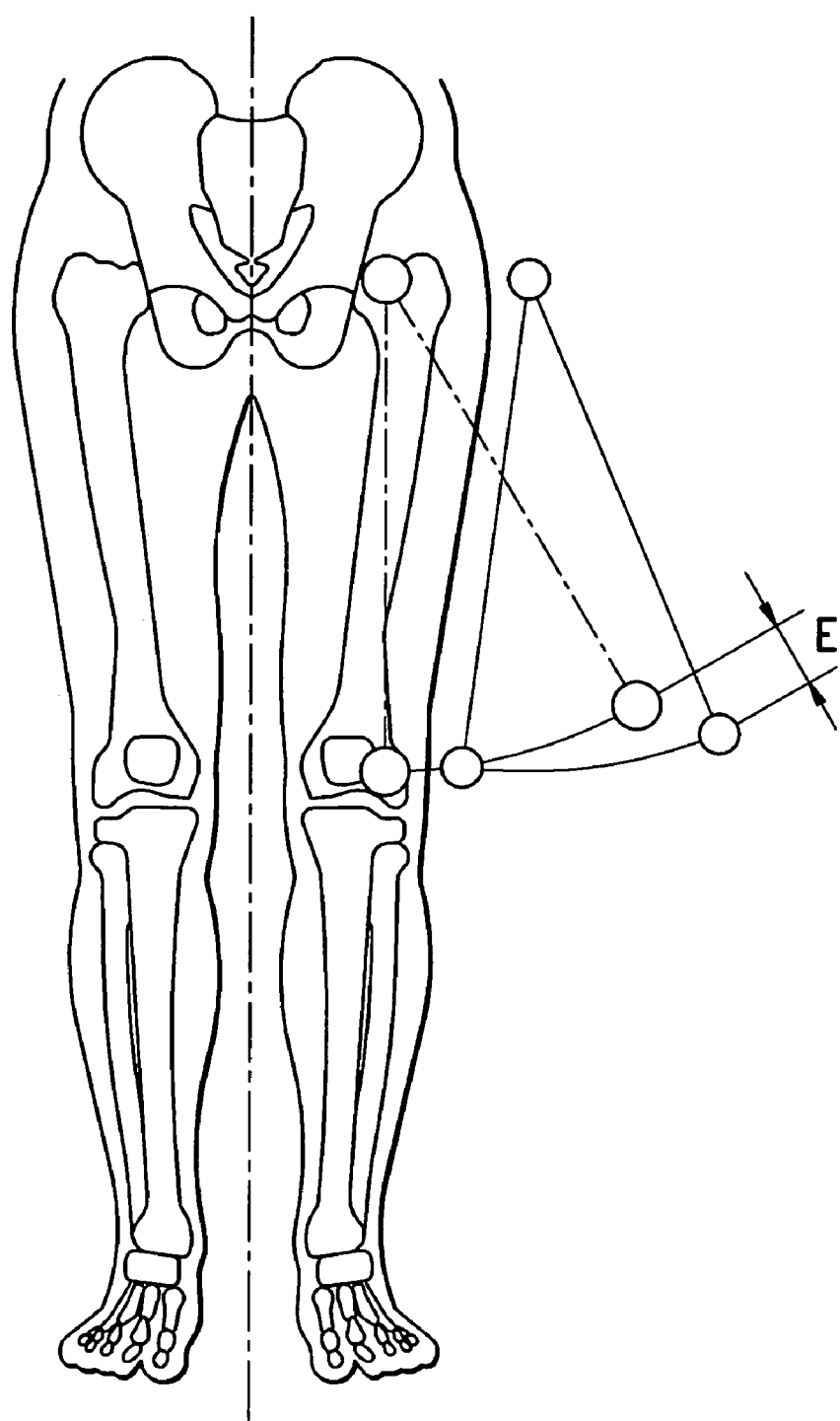
FIG. 6 is a view for explaining the difference in motion between the human body and the assisting device.

Additionally referring to FIG. 5, the drive unit 3 comprises a hip joint actuator 10 and a knee joint actuator 26, each consisting of an electric motor equipped with a reduction gear or the like, where the actuators are attached to either end of a link bar 25 (second linkage means). The drive unit 3 is adapted by using a well-known chucking mechanism so as to be able to repeatedly attached and detached with respect to the hip drive source mount 9 provided to the hip support member 1 at a position corresponding to a side of the hip joint as well as with respect to a knee drive source mount 27 provided to the lower leg support member 2 at a position corresponding to a side of the knee joint.

The link bar 25 comprises an outer tube 28 and an inner rod 29 telescopically connected so as to be slidable relative to each other to allow expansion and contraction of the distance between the actuators 10 and 26 (arrow E). Inside the outer tube 28 is disposed a tension coil spring (not shown in the drawings), for example, so that the spring is connected to the inner rod 29, upon which the weight of the knee joint actuator 26 is applied, to always exert a tensioning force upon the inner rod 29 in a direction to support the weight. In this way, the knee joint actuator 26 is pulled up toward the hip support member to decrease the force imposed upon the lower leg portion and at the same time prevent the lower leg support member 2 from slipping down inadvertently. It should be noted that the link bar 25 is formed along an arc of a constant curvature so as to extend along the side of the thigh.

A base portion 31 of the hip drive source mount 9 is attached to a vicinity of the rigid belt joint 13 (FIG. 2) via a link plate 30 (first linkage means) made of a flexible material such as an elastomeric material. The link plate 30 extends out from a side end portion of the back support 4 obliquely in a forward and downward direction, and mounted by bolts passed through elongated holes 61 so that the position of the link plate 30 can be adjustable. This allows a rotation center axis AM of the hip joint actuator 10 to coincide with the hip joint center P of the human body which can vary depending on the build of the user.

The link plate 30 is adapted, by adjusting the aspect ratio of its cross section, for example, such that the link plate 30 is hard to deform in the fore and aft direction as well as in the up and down direction to prevent deviation of the rotational center axis AM of the hip joint actuator 10 from the hip joint center P when the thigh is moved in the fore and aft direction (arrow S) to swing the link bar 25 in the fore and aft direction under the rotational force from the hip joint actuator 10, and such that the link plate 30 can undergo a bending deformation (arrow B) in the lateral direction (i.e., in a direction of an arc which is tangential to the rotational center axis AM of the hip joint actuator 10) and a torsional deformation (arrow T) which is a deformation around an axis AC perpendicular to the rotational center axis AM so as to accommodate a certain range of change in the axis orientation of the hip joint actuator 10 and allow the support member to follow the lateral motions and twisting motions of the thigh to a certain extent.

By imparting the above degree of freedom to the hip drive source mount 9 of the hip support member 1 as well as to the link bar 25 interconnecting the actuators 10 and 26 of the drive unit 3, the positions of the drive source mounts 9, 27 connected to the actuators 10, 26 can vary following the twisting movements and fore and aft or right and left swinging movements of the leg, to thereby avoid hampering the motion of the user's body. Because the axis of deformation AC of the link plate 30 is adjusted to cross the rotation center axis AM of the hip joint actuator 10, positional deviation of the hip joint actuator 10 with respect to the motion of the thigh can be minimized and the hip drive source mount 9 can be prevented from pushing or rubbing the user's body. The covers surrounding the link bar 25 and the link plate 30 are provided with accordion portions 62, 63 to accommodate the expansion and contraction of the link bar 25 as well as the bending and torsioning of the link plate 30.

If the device of the present invention is worn over a spat S for exercise that is adapted to provide a specific muscle(s) with a tightening force that is equivalent to that produced by taping (see Japanese Patent Application Laid-Open No. 2001-214303), the device can function even more effectively to improve the motion ability of the user in cooperation with the muscle support effect resulting from the tightening force produced by the fibers forming the spat S. Also, if the drive torque is effected in reverse, the device of the present invention can apply a load torque upon the joint, and therefore the device can be used not only as a motion assisting device but also as a load generator for medical treatment, rehabilitation or training for muscle development.

INDUSTRIAL APPLICABILITY

As described above, according to the present invention, the following advantages can be obtained:

1. Owing to the structure where the hip joint actuator is mounted to the body via a link plate serving as a first linkage means having at least two degrees of freedom, and the hip joint actuator and the knee joint actuator are connected to each other via a link bar serving as a second linkage means having an expandable and contractable means, deformation in lateral and torsional directions, for example, of the link plate and expansion/contraction of the link bar can absorb a deviation in position between the joints of the user's body and the associated actuators.
2. Owing to the structure where the spring means supports a weight of the knee joint rotational force generator and component parts below the knee joint rotational force generator, it is possible to exert a force from the spring means substantially comparable with the weight of the knee joint actuator to pull it up toward the hip whereby the force imposed upon the lower leg portion can be reduced and inadvertent slip of the support member fitted on the lower leg portion can be prevented.
3. Because the linkage between the hip joint actuator and the hip support member is embodied by using a flexible member accommodating a positional deviation of the hip joint actuator in a direction of an arc tangential to a rotation center axis of the hip joint actuator, and in a torsional direction around an axis perpendicular to the rotation center axis of the hip joint actuator, it is possible to mount the hip joint actuator to the body so as to be able to follow the torsional movements as well as fore and aft or right and left swinging movements of the hip joint.
4. Owing to the structure where an axis of deformation of the link plate for connecting the hip joint actuator to the hip support member crosses the rotation center axis of the hip joint actuator, it is possible to minimize a deviation of motion of the hip joint actuator with respect to the motion of the hip joint.

Thus, the walking assistance device of the present invention having adjustability and a plurality of degrees of freedom can solve the prior art problem of hampering the free motion of body worn on the user.

The invention claimed is:

1. A walking assistance device, comprising:
    a hip support member configured to be worn on a hip of a user;
    a hip joint rotational force generator mounted on the hip support member at a point corresponding to a hip joint of the user;
    a link bar comprising a base end attached to an output end of the hip joint rotational force generator for a powered pivotal movement around a rotational center line of the hip joint rotational force generator;
    a knee joint rotational force generator mounted on a free end of the link bar at a point corresponding to a knee joint of the user; and
    a lower leg support member attached to an output end of the knee joint generator for a powered pivotal movement around a rotational center line of the knee joint rotational force generator,
    wherein the hip joint rotational force generator is hinged to the hip support member so as to accommodate a lateral movement of the hip joint rotational force generator, and
    wherein the link bar is configured to be extended and retracted.

2. The walking assistance device according to claim 1, wherein the lateral movement is effected around a hinge axis perpendicular to the rotational center line of the hip joint rotational force generator.

3. The walking assistance device according to claim 1, wherein the link bar comprises a spring member configured to resiliently urge the free end of the link bar toward the base end thereof.

4. The walking assistance device according to claim 1, wherein the hip joint rotational force generator is mounted on the hip support member so as to accommodate a torsion movement of the hip joint rotational force generator around an axial line perpendicular to the rotational center line of the hip joint rotational force generator.

5. The walking assistance device of claim 1, wherein the hip joint rotational force generator comprises an actuator, and wherein the actuator comprises an electric motor.

6. The walking assistance device of claim 1, wherein the knee joint rotational force generator comprises an actuator, and wherein the actuator comprises an electric motor.

7. The walking assistance device of claim 1, wherein the knee joint rotational force generator is further configured to attach only at or above an upper part of the Achilles tendon.

* * * * *